United States Patent
Butt et al.

(10) Patent No.: US 12,204,180 B2
(45) Date of Patent: Jan. 21, 2025

(54) BIOMARKER-RESPONSIVE CONTACT LENS

(71) Applicant: Khalifa University of Science and Technology, Abu Dhabi (AE)

(72) Inventors: Haider Butt, Abu Dhabi (AE); Mohamed Elsherif, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 524 days.

(21) Appl. No.: 17/693,493

(22) Filed: Mar. 14, 2022

(65) Prior Publication Data
US 2023/0314839 A1  Oct. 5, 2023

(51) Int. Cl.
*G02C 7/04* (2006.01)
*A61B 5/00* (2006.01)

(52) U.S. Cl.
CPC ............ *G02C 7/049* (2013.01); *A61B 5/6821* (2013.01); *G02C 7/042* (2013.01)

(58) Field of Classification Search
CPC .... G02C 7/049; G02C 7/042; G02C 2202/10; G02C 7/04; A61B 5/6821; A61B 5/14555
See application file for complete search history.

(56) References Cited

U.S. PATENT DOCUMENTS

| | | |
|---|---|---|
| 8,385,998 B2 | 2/2013 | Zhang et al. |
| 2020/0038173 A1* | 2/2020 | Reedy ............... G02C 7/044 |

FOREIGN PATENT DOCUMENTS

EP  0458508 A2  11/1991

OTHER PUBLICATIONS

"Abbott a Promise for Life", 13 pages.
"Guardian Telemetered Glucose Monitoring System (TGMS)", FDA U.S. Food & Drug Administration, 3 pages.
Abreu, Catarina M., et al., "Emerging Biosensing Technologies for Neuroinflammatory and Neurodegenerative Disease Diagnostics", Biosensors for Neuroinflammatory and Neurodegenerative Disease Diagnostics, May 2018, vol. 11, Article 164, 13 pages.
Alexeev, Vladimir L., et al., "High Ionic Strength Glucose-Sensing Photonic Crystal", Anal. Chem. 2003, 75, 2316-2323.
Alexeev, Vladimir L. , et al., "Photonic Crystal Glucose-Sensing Material for Noninvasive Monitoring of Glucose in Tear Fluid", Clinical Chemistry 50:12, 2353-2360, (2004).
Aller, Thomas A., "Myopia Control with Bifocal Contact Lenses: A Randomized Clinical Trial", Optometry and Vision Science, vol. 93, No. 4, Apr. 2016.

(Continued)

*Primary Examiner* — James C. Jones
(74) *Attorney, Agent, or Firm* — Billion & Armitage

(57) ABSTRACT

Embodiments of the present disclosure describe a biomarker-responsive bifocal contact lens comprising a monovision contact lens having a first focal length and a Fresnel contact lens having a second focal length, wherein the Fresnel contact lens comprises a biomarker-responsive hydrogel, and wherein the Fresnel contact lens is disposed on an outer surface of the monovision contact lens, wherein an optical characteristic of the Fresnel contact lens changes in response to the biomarker concentration in the ocular fluid.

20 Claims, 20 Drawing Sheets

(56) References Cited

OTHER PUBLICATIONS

Badugu, Ramachandram, et al., "A glucose-sensing contact lens: from bench top to patient", Current Opinion in Biotechnology 2005, 16:100-107.
Badugu, Ramachandram, et al., "Noninvasive Continuous Monitoring of Physiological Glucose Using a Monosaccharide-Sensing Contact Lens", Anal. Chem. 2004, 76, 610-618.
Blum, Alyson, "Freestyle Libre Glucose Monitoring System", Clinical.DiabetesJournals.org, vol. 36, No. 2, Spring 2018, 203-204.
Böhm, Daniel, et al., "Comparison of tear protein levels in breast cancer patients and healthy controls using a de novo proteomic approach", Oncology Reports 28: 429-438, 2012.
Chalmers, Robin L., et al., "Dryness symptoms among an unselected clinical population with and without contact ens wear", Contact Lens & Anterior Eye 29 (2006) 25-30.
Chen, Liyan, et al., "Characterization of The Human Tear Metabolome by LC-MS/MS", J. Proteome Res. 2011, 10, 4876-4882.
Chu, Ming Xing, et al., "Soft contact lens biosensor for in situ monitoring of tear glucose as non-invasive blood sugar assessment", Talanta 83 (2011) 960-965.
Cohen, Allen Louis, "Diffractive Bifocal Lens Designs", symposium paper, vol. 70, No. 6, pp. 461-468.
Comoglu, Selim Selcuk, et al., "Tear levels of tumor necrosis factor-alpha in patients with Parkinson's disease", Neuroscience Letters 553 (2013) 63-67.
Danne, Thomas, et al., "International Consensus on Use of Continuous Glucose Monitoring", Diabetes Care vol. 40, Dec. 2017, 1631-1640.
Domschke, Angelika, et al., "Holographic Sensors in Contact Lenses for Minimally-Invasive Glucose Measurements", 1320-1323.
Elsherif, Mohamed, et al., "Glucose Sensing with Phenylboronic Acid Functionalized Hydrogel-Based Optical Diffusers", ACS Nano 2018, 12, 2283-2291.
Elsherif, Mohamed, et al., "Hydrogel optical fibers for continuous glucose monitoring", Biosensors and Bioelectronics 137 (2019) 25-32.
Elsherif, Mohamed, et al., "Wearable Contact Lens Biosensors for Continuous Glucose Monitoring Using Smartphones", ACS Nano 2018, 12, 5452-5462.
Gabai, Rachel, et al., "Characterization of the Swelling of Acrylamidophenylboronic Acid-Acrylamide Hydrogels upon Interaction with Glucose by Faradaic Impedance Spectroscopy, Chronopotentiometry, Quartz-Crystal Microbalance (QCM), and Surface Plasmon Resonance (SPR) Experiments", J. Phys. Chem. B 2001, 105, 8196-8202.
Ghormley, N. Rex, "The Hydron Echelon Bifocal Contact Lens", vol. 16, Nos. 11 & 12, Nov./Dec. 1989.
Johnson, Heidi, "The Effect of the Echelon Bifocal Contact Lens on Contrast Sensitivity and Brightness Acuity Testing", 7 pages.
Kabilan, S., et al., "Glucose-sensitive holographic sensors", Journal of Molecular Recognition, J. Mol. Recognit. 2004; 17: 162-166.
Kabilan, Satyamoorthy, et al., "Holographic glucose sensors", Biosensors and Bioelectronics 20 (2005) 1602-1610.
Keum, Do Hee, et al., "Wireless smart contact lens for diabetic diagnosis and therapy", Sci. Adv. 2020; 6: eaba3252, Apr. 24, 2020, 12 pages.
Kim, Sangjoon, et al., "Polyacrylamide Hydrogel Properties for Horticultural Applications", International Journal of Polymer Anal. Charact., 15: 307-318, 2010.
Kim, Joohee, et al., "Recent Advances in Smart Contact Lenses", Adv. Mater. Technol. 2020, 5, 1900728, 17 pages.
Kim, Joohee, et al., "Wearable smart sensor systems integrated on soft contact lenses for wireless ocular diagnostics", Nature Communications, Apr. 27, 2017, 8 pages.
Ku, Minjae, et al., "Smart, soft contact lens for wireless immunosensing of cortisol", Sci. Adv., 6: eabb2891, Jul. 8, 2020, 10 pages.
Lane, Jennifer D., et al., "Tear Glucose Dynamics in Diabetes Mellitus", Current Eye Research, 31:895-901, 2006.
Li, Xueming, et al., "Stretchable Binary Fresnel Lens for Focus Tuning", Scientific Reports, May 3, 2016, 8 pages.
Mamkin, Irene, et al., "Real-Time Continuous Glucose Monitoring in the Clinical Setting: The Good, the Bad, and the Practical", J Diabetes Sci Technol vol. 2, Issue 5, Sep. 2008, 8 pages.
March, Wayne, et al., "Fluorescent Measurement in the Non-Invasive Contact Lens Glucose Sensor", Diabetes Technology & Therapeutics, vol. 8, No. 3, 2006, 312-317.
McGarraugh, Geoffrey, et al., "FreeStyle Navigator Continuous Glucose Monitoring System with TRUstart Algorithm, a 1-Hour Warm-Up Time", Journal of Diabetes Science and Technology, vol. 5, Issue 1, Jan. 2011, 99-106.
Miller, O.E., et al., "Thin Sheet Plastic Fresnel Lenses of High Aperture", Journal of the Optical Society of America, vol. 41, No. 11, Nov. 1951, 807-815.
Moreddu, Rosalia, et al., "Contact Lens Technology: From Fundamentals to Applications", Adv. Healthcare Mater. 2019, 8, 1900368, 24 pages.
Moreddu, Rosalia, et al., "Contact lenses for continuous corneal temperature monitoring", RSC Adv., 2019, 9, 11433-11442.
Moreddu, Rosalia, et al., "Integration of paper microfluidic sensors into contact lenses for tear fluid analysis", Lab Chip, 2020, 20, 3970-3979.
Moreddu, Rosalia, et al., "Laser-inscribed contact lens sensors for the detection of analytes in the tear fluid", Sensors & Actuators: B. Chemical 317 (2020) 128183, 9 pages.
Mrugacz, Malgorzata, "CCL4/MIP-1β Levels in Tear Fluid and Serum of Patients with Cystic Fibrosis", Journal of Interferon & Cytokine Research, vol. 30, No. 7, 2010, 509-512.
Park, Sejin, et al., "Electrochemical non-enzymatic glucose sensors", Analytica Chimica Acta 556 (2006) 46-57.
Park, Jihun, et al., "Soft, smart contact lenses with integrations of wireless circuits, glucose sensors, and displays", Sci. Adv. 2018;4: eaap9841, Jan. 24, 2018, 11 pages.
Reddy, Nihaal, et al., "Monitoring Technologies- Continuous Glucose Monitoring, Mobile Technology, Biomarkers pf Glycemic Control", NCBI Bookshelf, Aug. 16, 2020, 46 pages.
Rentka, Aniko, et al., "Membrane array and multiplex bead analysis of tear cytokines in systemic sclerosis", Immunol Res, 64:619-626, Dec. 2015.
Riaz, Rafia Sarah, et al., "Anthocyanin-Functionalized Contact Lens Sensors for Ocular pH Monitoring", ACS Omega, 4, 21792-21798, Dec. 12, 2019.
Rodbard, David, "Continuous Glucose Monitoring: A Review of Successes, Challenges, and Opportunities", Diabetes Technology & Therapeutics, vol. 18, Supplement 2, 2016, 25 pages.
Saeedi, E., et al., "Self-assembled crystalline semiconductor optoelectronics on glass and plastic", J. Micromech. Microeng. 18 (2008) 075019, 8 pages.
Tierney, M.J., et al., "Clinical evaluation of the GlucoWatch® biographer: a continual, non-invasive glucose monitor for patients with diabetes", Biosensors & Bioelectronics 16 (2001) 621-629.
Toshida, Hiroshi, et al., "Bifocal contact lenses: History, types, characteristics, and actual state and problems", Clinical Ophthalmology 2008:2(4) 869-877.
Tseng, Ryan Chang, et al., "Contact-Lens Biosensors", Sensors 2018, 18, 2651; doi:10.3390/s18082651.
Vázquez, Rebeca Martinez, et al., "Fabrication of binary Fresnel lenses in PMMA by femtosecond laser surface ablation", Jun. 6, 2011 / vol. 19, No. 12 / Optics Express 11597-11604.
Versura, Piera, et al., "Diagnostic performance of a tear protein panel in early dry eye", Molecular Vision 2013; 19:1247-1257 <http://www.molvis.org/molvis/v19/1247>.
Welsh, John B., et al., "Accuracy, Utilization, and Effectiveness Comparisons of Different Continuous Glucose Monitoring Systems", Diabetes Technology & Therapeutics, vol. 21, No. 3, 2019, 8 pages.
Yang, Wenqian, et al., "A Novel Type of Fluorescent Boronic Acid That Shows Large Fluorescence Intensity Changes Upon Binding with a Carbohydrate in Aqueous Solution at Physiological pH", Bioorganic & Medicinal Chemistry Letters 13 (2003) 1019-1022.

(56) References Cited

OTHER PUBLICATIONS

Yetisen, Ali Kemal, "Holographic Sensors", Springer Theses, Recognizing Outstanding Ph.D. Research Holographic, Nov. 2014, 175 pages.

* cited by examiner

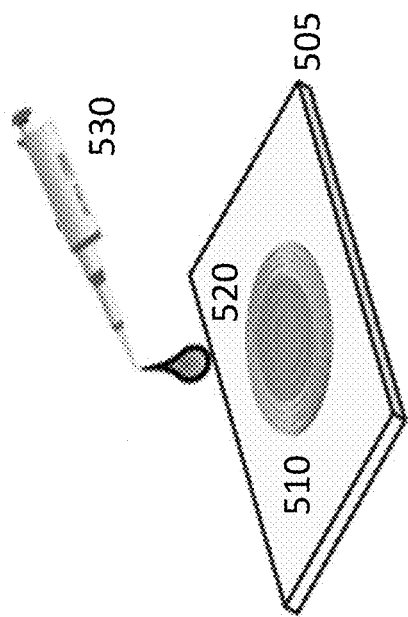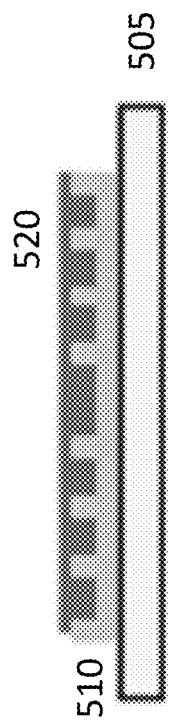
FIG. 6A
FIG. 6B

BIOMARKER-RESPONSIVE CONTACT LENS

BACKGROUND

Commercial implantable biomarker monitoring devices are invasive and uncomfortable. For example, commercial continuous glucose monitoring devices (CGM) detect glucose concentrations in the interstitial fluid, which require the insertion of an electrochemical probe through the skin. This transdermal insertion often causes pain or discomfort to the user. On the contrary, tears are easily accessible and can be collected or measured in a minimally invasive manner. Tears are interstitial fluid and could be used as a blood proxy for diagnosing cancer, Alzheimer's disease, Parkinson's disease, cystic fibrosis, glaucoma, diabetes, and various other diseases. In this context, contact lens-integrated sensors that sample and measure tears offer a minimally invasive and continuous diagnostic platform to detect numerous biomarkers.

However, contact lens-integrated sensors suffer from a number of drawbacks. Electrochemical contact lens sensors suffer degradation in a short lifespan and require a power supply to drive the chemical reaction. Fluorescent contact lens sensors are unstable and produce unpredictable results under changing conditions. And finally, light diffractive contact lens sensors have been limited to monovision contact lenses.

The common vision errors (myopia, hyperopia, and presbyopia) affect millions of the world population and controlling such refractive errors by the monovision contact lenses does not stop their progression. For example, myopia was found to progress yearly with −0.5 diopter when the subjects were using the traditional monovision contact lenses. Bifocal contact lenses have been known for controlling myopia, decreasing its progression by 84% for individuals of ages 9-40 years. Additionally, bifocal contact lenses are prescribed for people suffer age-related decline in near vision (presbyopes). Hence, it is desirable to develop bifocal contact lenses capable of tear analysis and biomarker detection.

SUMMARY

In general, embodiments of the present disclosure describe a biomarker-responsive bifocal contact lens comprising a monovision contact lens having a first focal length and a Fresnel contact lens having a second focal length, wherein the Fresnel contact lens comprises a biomarker-responsive hydrogel, and wherein the Fresnel contact lens is disposed on an outer surface of the monovision contact lens, wherein an optical characteristic of the Fresnel contact lens changes in response to the biomarker concentration in the ocular fluid.

Embodiments of the present disclosure further describe a method of manufacturing a biomarker-responsive bifocal contact lens comprising the steps of: providing a Fresnel lens mold, casting a biomarker-responsive hydrogel on the Fresnel lens mold, polymerizing the biomarker-responsive hydrogel, removing the biomarker-responsive hydrogel from the Fresnel lens mold, and combining the biomarker-responsive hydrogel to a monovision contact lens.

Another embodiment of the present disclosure is a method of measuring a biomarker concentration using a biomarker-responsive bifocal contact lens comprising: placing the biomarker-responsive bifocal contact lens on an eye of a patient, the biomarker-responsive bifocal contact lens comprising a monovision contact lens having a first focal length and a Fresnel contact lens having a second focal length, wherein the Fresnel contact lens is formed from a biomarker-responsive hydrogel; operating a light source at an angle θ incident to the contact lens, wherein a laser beam hits the contact lens as the angle θ and reflects off of the contact lens; collecting a reflected light beam in a photodetector; measuring an optical characteristic of the reflected light beam; and calculating the biomarker concentration.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 6A is a perspective view of a biomarker-responsive hydrogel cast onto a Fresnel lens mold, according to one or more embodiments of the present disclosure.

FIG. 6B is a cross-sectional view of a biomarker-responsive hydrogel cast onto a Fresnel lens mold, according to one or more embodiments of the present disclosure.

DETAILED DESCRIPTION

The present disclosure is directed to the structure of a biomarker-responsive bifocal contact lens and methods of tear analysis. According to one or more embodiments in the present disclosure, the biomarker-responsive contact lens is capable of non-invasive and continuous analysis of interstitial fluid. In some embodiments, the biomarker-responsive contact lens can monitor glucose concentrations for diabetic patients.

The biomarker-responsive contact lens has two focal lengths: a near-field focal length due to a Fresnel contact lens, and a far-field focal length due to the curvature of a monovision contact lens. Bifocal contact lenses have been known for controlling myopia progression and are also effective at slowing age-related decline in near vision (presbyopes).

Figure 1A:
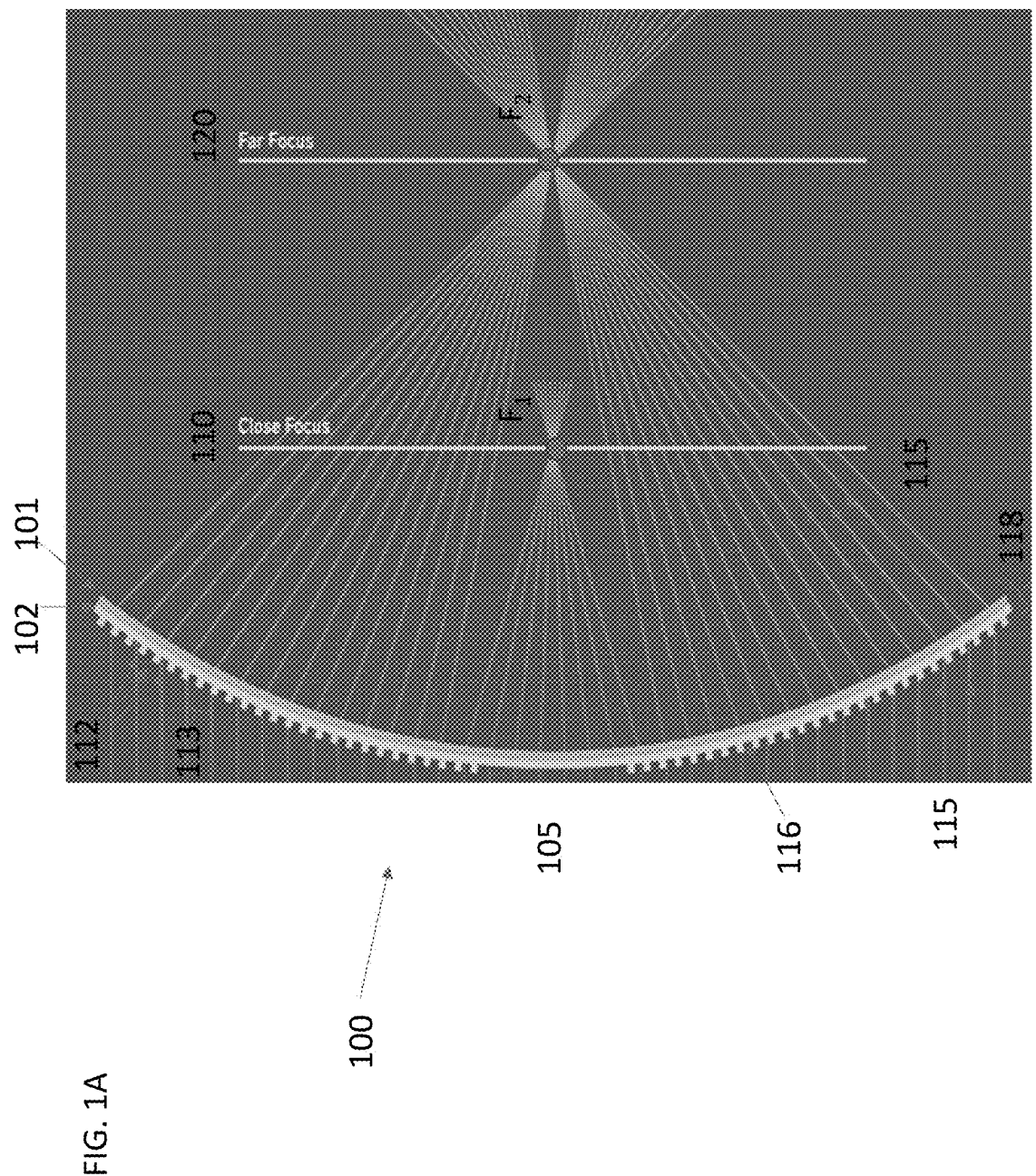
FIG. 1A is a cross-sectional view of a biomarker-responsive bifocal contact lens operating in a low biomarker concentration, according to one or more embodiments of the present disclosure.

FIG. 1A is a cross-sectional view of a biomarker-responsive bifocal contact lens 100 operating in a low biomarker concentration. The term "biomarker" refers to a measurable substance in a human whose presence is indicative of some phenomenon such as disease, infection, or environmental exposure. The biomarker-responsive bifocal contact lens comprises a monovision contact lens 101 and a Fresnel contact lens 102. The term "Fresnel" refers to a lens structure comprising a plurality of concentric rings. Fresnel contact lens 102 comprises a plurality of concentric rings 112 with a groove depth 116, separation distance 113, and a central zone 105. Fresnel contact lens 102 has a thickness 118. FIG. 1A illustrates a plurality of light rays 115 entering the biomarker-responsive bifocal contact lens and converging at focal point 1 ($F_1$) at a distance 110 and converging at focal point 2 ($F_2$) at a distance 120.

The elements that compose the physical structure of the lens (groove depth, number of rings, groove spacing, and total thickness) are referred to as the "optical features" of the lens 100. The term "optical performance" refers to any of the following optical properties of the lens: transmitted optical power, reflected optical power, near field focal length, far field focal length, light focusing efficiency, and/or refractive index. The optical features of the contact lens 100 (such as the plurality of concentric rings 112, groove depth 116, number of concentric rings, separation distance 113, size of central zone 105, and thickness 118) affect the optical performance of the lens. In other words, any change to the optical properties of the lens will affect the optical performance. The term "optical characteristic" refers to any optical feature or any optical performance element described above.

In this embodiment, light rays 115 are moving toward contact lens 100. Light rays 115 first contact the Fresnel contact lens 102, and next contact the monovision contact lens 101. A majority of light rays 115 are refracted by contact lens 100 and pass through to a patient's eye (not shown here). Biomarker-responsive bifocal contact lens causes light rays 115 to converge on $F_1$ at a distance 110 and causes light rays 115 to converge on $F_2$ at a distance 120. Contact lens 100 has two focal lengths, $F_1$ and $F_2$, meaning contact lens 100 is bifocal. Bifocal contacts are desirable because they can control myopia, presbyopes, and progressive decline in vision. Central zone 105 is designed for clear vision at far distances, with the Fresnel structure designed for near-viewing.

A Fresnel structure enables the construction of lenses of large aperture and short focal length without the mass and volume of material that would be required by a lens of conventional design. In this embodiment, the elements of the Fresnel structure change in response to biomarker presence in the patient's eye. The elements of the Fresnel structure comprise the following: groove depth 116 is the distance that a concentric ring protrudes out of the Fresnel structure; separation distance 113 is the distance that adjacent concentric rings 112 are separated by; central zone 105 is the center area of contact lens 100 that does not contain any concentric rings; and thickness 118 is the thickness of the Fresnel contact lens 102.

It is important to note that each of the plurality of concentric rings do not have identical groove depth 116 or separation distance 113. Groove depth 116 and separation distance 113 may differ between each of the plurality of concentric rings 112.

The elements of the Fresnel structure (groove depth 116, separation distance 113, central zone 105, and thickness 118) give the Fresnel contact lens 102 increased responsiveness to biomarker concentration. Traditional monovision contact lenses lack concentric rings, groove depth, and separation distance, and therefore, the optical characteristics of monovision contact lens are less responsive to changes in biomarker concentration. Contact lens 100 with the Fresnel structure can function in lower-biomarker concentrations than traditional monovision lenses.

Figure 1B:
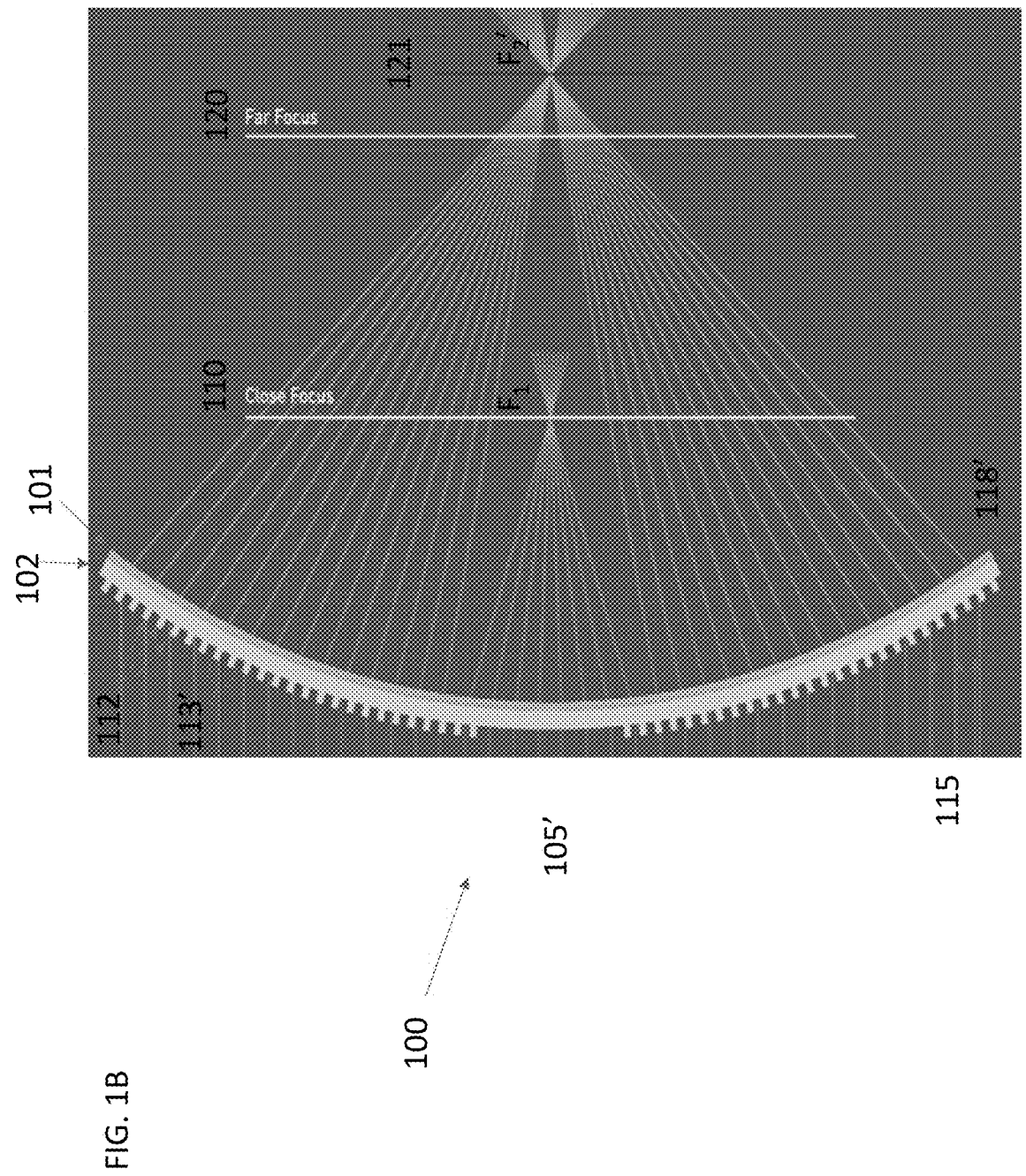
FIG. 1B is a cross-sectional view of a biomarker-responsive bifocal contact lens operating in a high biomarker concentration, according to one or more embodiments of the present disclosure.

FIG. 1B is an illustration of the biomarker-responsive bifocal contact lens 100 operating in a high biomarker concentration. In the high biomarker concentration, Fresnel contact lens 102 comprises a plurality of concentric rings 112 with a groove depth 116' with a separation distance 113' and a central zone 105'. Fresnel contact lens 102 has a thickness 118'. FIG. 1B illustrates a plurality of light rays 115 entering the biomarker-responsive bifocal contact lens and converging at $F_1$ at a distance 110 and converging at $F_2'$ at a distance 121.

FIG. 1B illustrates the biomarker-responsive bifocal contact lens' response to high biomarker concentrations. Fresnel contact lens 102 swells in high biomarker concentrations, and the thickness 118' of the Fresnel contact lens 102 increases (118'>118). The plurality of concentric rings 112 with groove depth 116', separation distance 113', and central zone 105' change in response to biomarker concentration, altering the optical characteristics of the biomarker-responsive contact lens. The optical properties of the lens 100 are altered by the glucose concentrations, which affects the optical performance of the lens 100. In particular, changes to the optical properties of the lens (groove depth, thickness, separation distance, number of concentric zones) result in changes to the refractive index of contact lens 100, resulting in an increased $F_2$ (distance 121>distance 120).

Figure 2A:
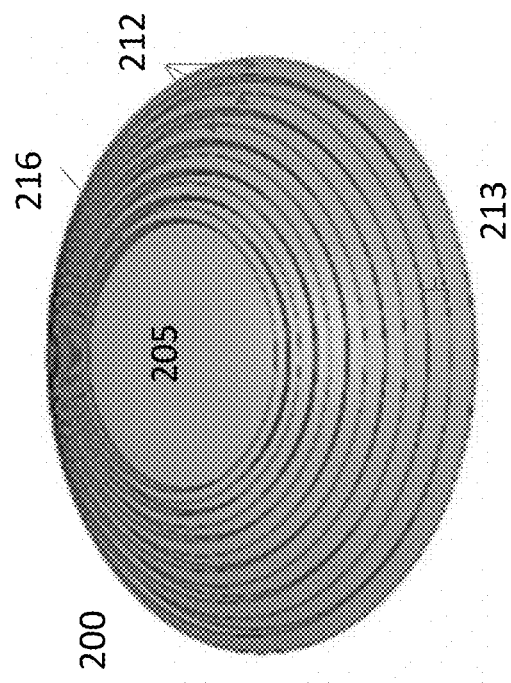
FIG. 2A is a perspective view of a glucose-responsive bifocal contact lens in glucose-free tears, according to one or more embodiments of the present disclosure.
Figure 2B:
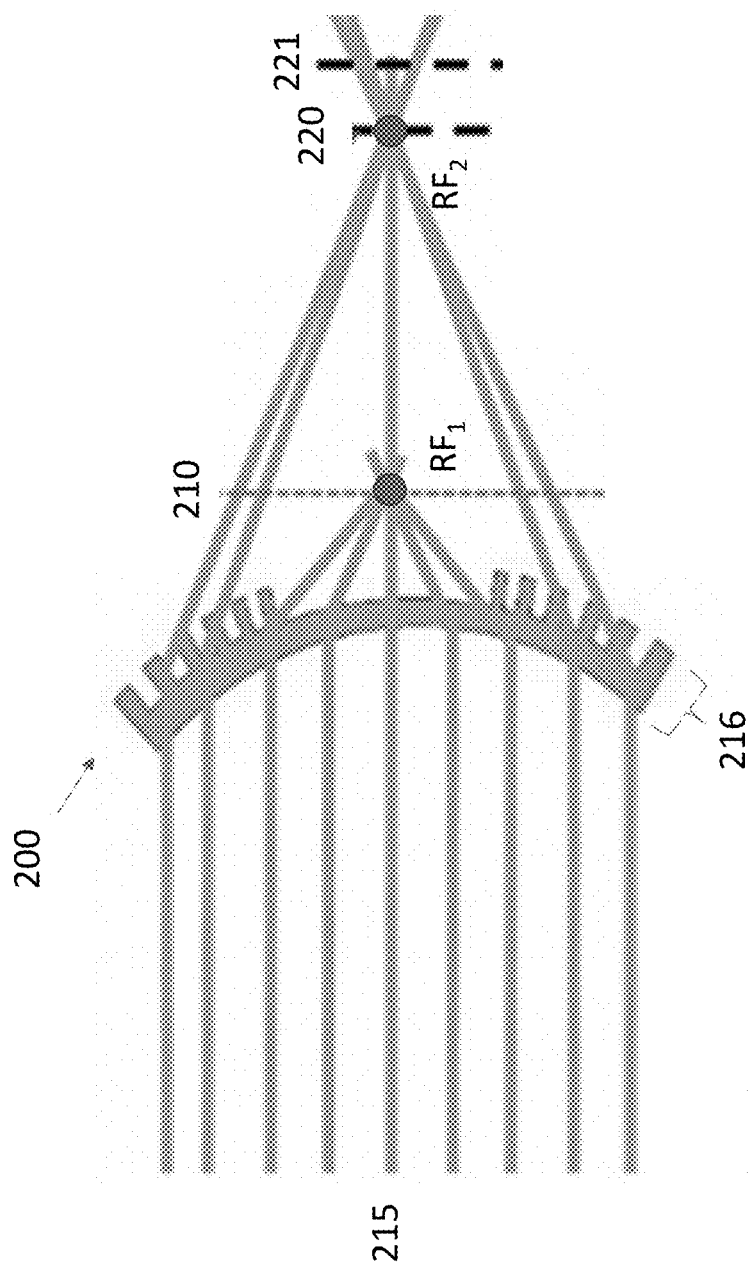
FIG. 2B is a cross-sectional view of a glucose-responsive bifocal contact lens in glucose free tears with near-field and far-field focal length illustrations, according to one or more embodiments of the present disclosure.
Figure 2C:
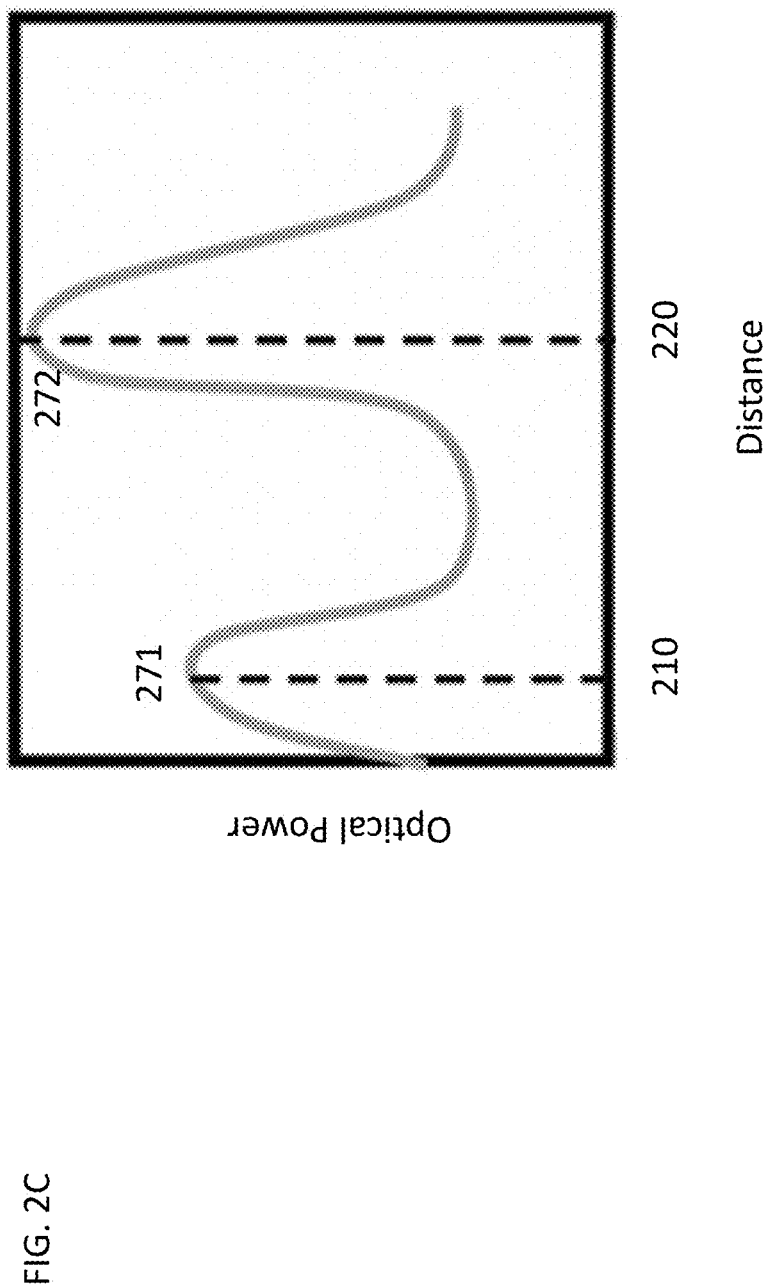
FIG. 2C is a graphical illustration of optical power measurements of the glucose-responsive contact lens in glucose free tears, according to one or more embodiments of the present disclosure.
Figure 3A:
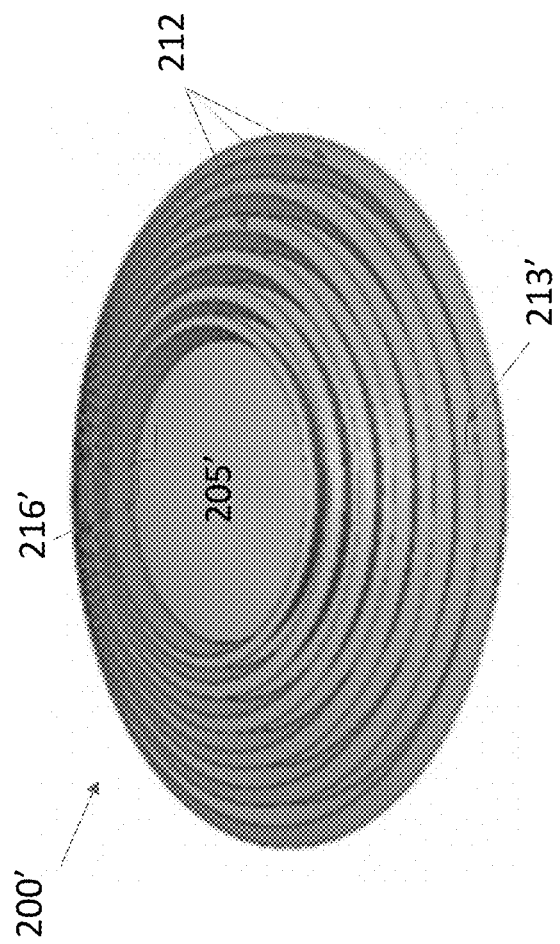
FIG. 3A is a perspective view of a glucose-responsive bifocal contact lens in glucose-present tears, according to one or more embodiments of the present disclosure.
Figure 3B:
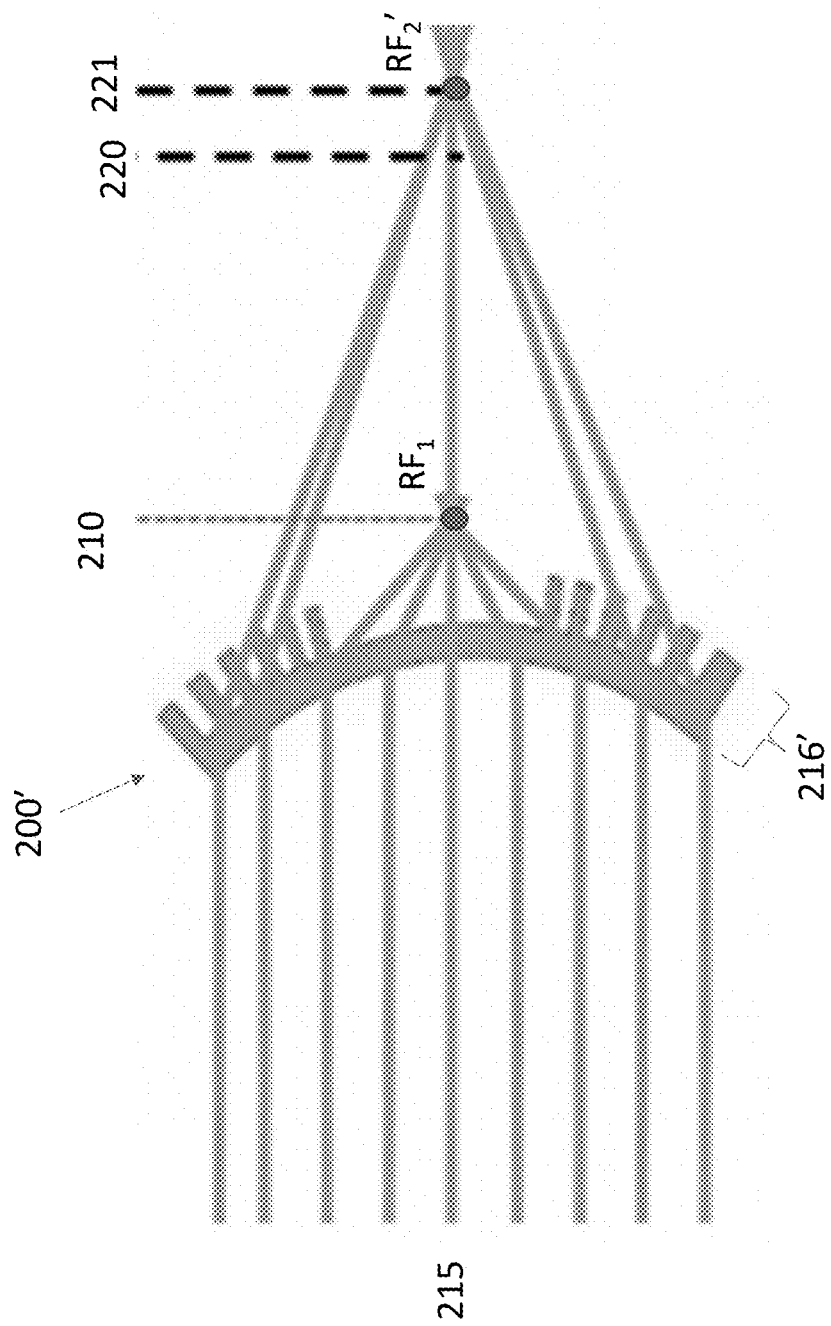
FIG. 3B is a cross-sectional view of a glucose-responsive bifocal contact lens in glucose-present tears with near-field and far-field focal length illustrations, according to one or more embodiments of the present disclosure.
Figure 3C:
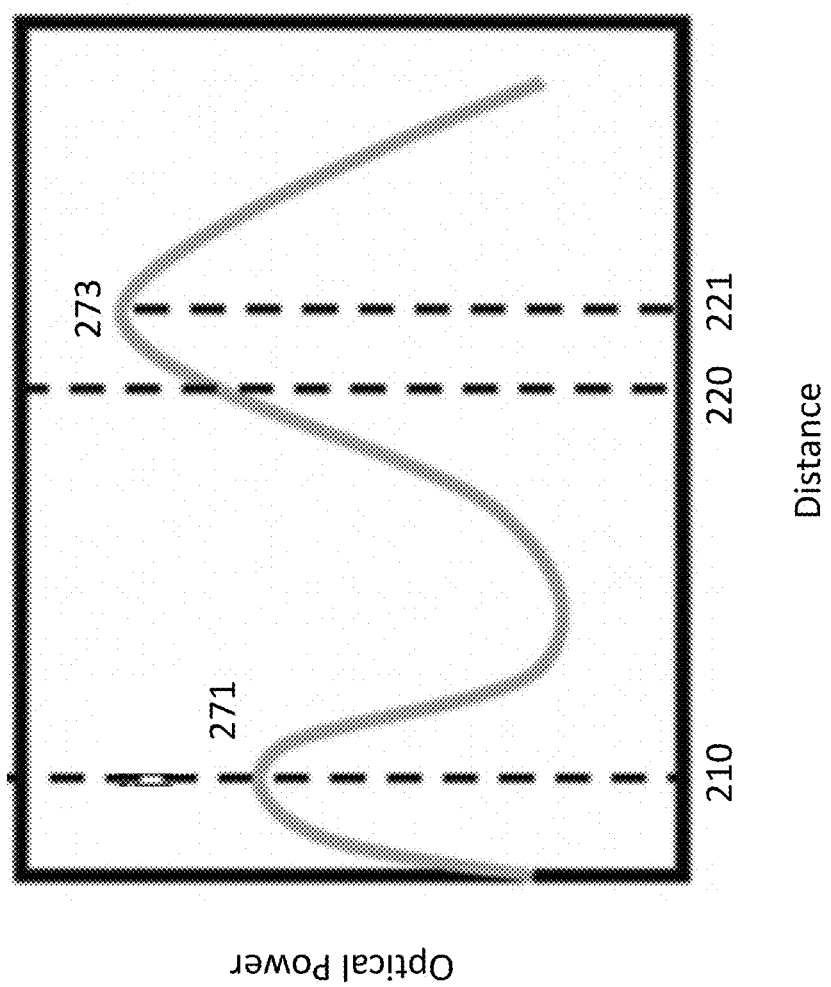
FIG. 3C is a graphical illustration of optical power measurements of the glucose-responsive contact lens in glucose-present tears, according to one or more embodiments of the present disclosure.

In the embodiment shown in FIGS. 2A-3C, a glucose-responsive bifocal contact lens 200 is illustrated. In FIGS. 2A-2C, contact lens 200 operates in glucose-free tears (tears not shown in this view). In FIGS. 3A-3C, contact lens 200' operates in glucose-including tears. FIGS. 2A-2C can be compared to FIGS. 3A-3C to illustrate the structural and optical response to changes in glucose concentration.

In one embodiment, glucose-responsive bifocal contact lens 200 is made from hydrogel and a phenylboronic acid (PBA) derivative, with contact lens 200 comprising a PBA concentration of 20 mol %. PBA derivatives may be covalently immobilized in a hydrogel matrix. Glucose is an important biomarker in monitoring diabetes, and therefore, developing a glucose-responsive monitoring system is highly desirable. In some embodiments, the concentration of PBA in the hydrogel is in the range of 12 mol % to 25 mol %. In other embodiments, different glucose-responsive compounds may be immobilized in a hydrogel matrix and formed into a Fresnel structure.

The lens 200 is designed to operate at the physiological pH (7.4), which is lower than the pKa of the utilized boronic acid, 3-(acrylamido) phenylboronic acid (pKa=8.5) when it is incorporated in the polyacrylamide hydrogel. At low pH, PBA exists in an uncharged trigonal planar form that reacts with glucose forming cyclic ester of pKa less than the physiological pH, subsequently it dissociates into a hydrogen ion and a stable boronate anion. While at high pH>pKa, the trigonal configuration of PBA dissociates donating a proton to constitute a stable tetrahedral anion, which has high affinity and stability to bind with glucose.

In the embodiment shown in FIG. 2A, a glucose-responsive bifocal contact lens 200 operates in glucose-free tears. Glucose-response bifocal contact lens 200 comprises a central zone 205, a plurality of concentric rings 212, a groove depth 216, and a separation distance 213. Glucose-response bifocal contact lens 200 has a total thickness 219. Glucose-responsive bifocal contact lens 200 has a substantially domed shape such that the contact lense will fit the curvature of a patient's eye.

FIG. 2B illustrates a cross-sectional view of a glucose-responsive bifocal contact lens 200 in glucose free tears, with $F_1$ at distance 210 from the contact lens and $F_2$ at distance 220 from the contact lens. Incident light rays 215 are reflected by the contact lens 200 and converge at reflected focal points $RF_1$ (at a distance 210) and $RF_2$ (at a distance 220).

FIG. 2C is a graphical illustration of the reflected optical power of the glucose-responsive bifocal contact lens 200 as a function of distance. Peaks 271 and 272 correspond to $RF_1$ and $RF_2$, respectively. If, for example, the refractive index of contact lens 200 decreases in response to an increase in glucose concentration, $RF_2$ will shift in response from a distance 220 to a distance 221 (see FIG. 3B and FIG. 3C below), and peak 272 will also shift.

Figure 9:
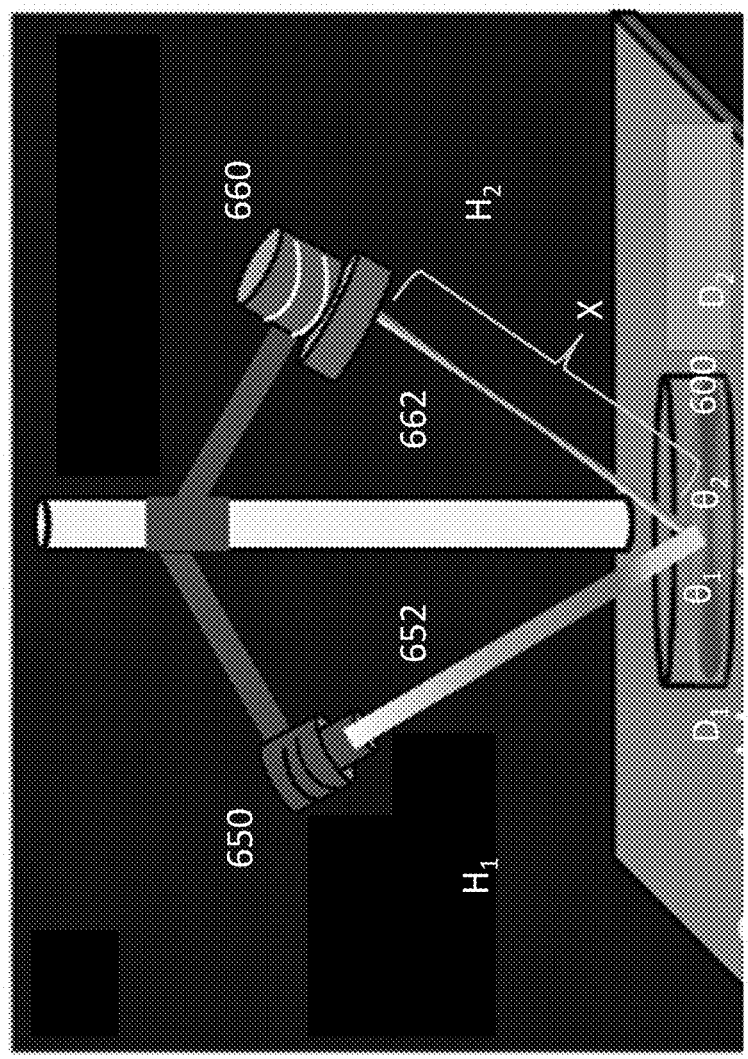
FIG. 9 is a simplified illustration of a method of measuring a biomarker concentration using a biomarker-responsive bifocal contact lens, according to one or more embodiments of the present disclosure.

Methods of measuring reflected optical power as a function of distance are further discussed in FIG. 9. FIG. 2C is merely included to show the correlation between reflected optical power as a function of distance.

In the embodiment shown in FIG. 3A, a glucose-responsive bifocal contact lens 200' operates in tears with a glucose concentration above 8 (mM). Glucose molecules bind with the glucose-responsive hydrogel and cause the contact lens to become hydrated (see FIG. 4). Due to the presence of glucose in the tears, the glucose-responsive bifocal contact lens 200' swells (see FIG. 4 for illustration on swelling). The total thickness of contact lens 200' increases to 219', the groove depth increases to 216', and the separation distance increases to 213' (as compared to contact lens 200 operating in glucose-free tears). It is important to note that changes in the physical structure between contact lens 200 and contact lens 200' are small—for instance, the total thickness 219 and 219' can differ in the range of 1-100 nm.

FIG. 3B illustrates a cross-sectional view of a glucose-responsive bifocal contact lens 200' in glucose-including tears (tears not shown in this view). Due to the presence of glucose in the tears, which cause thickness, groove depth, and separation distance of contact lens 200' to increase, the optical characteristics of the contact lens are altered. This subsequently decreases the refractive index of contact lens 200', modifying the focusing efficiency and focal length of contact lens 200'. $RF_2$ increases to a distance 221.

FIG. 3C is a graphical illustration of the reflected optical power of the glucose-responsive bifocal contact lens 200' as a function of distance. Due to the higher concentration of glucose, the refractive index of contact lens 200' decreases, modifying the focusing efficiency and focal length of contact lens 200'. Focal length of a Fresnel lens is governed by the following equation:

$$f = R^2/2m\lambda \qquad \text{Equation I}$$

where f is the focal length, R is the outer radius of the concentric ring zones, m is the number of the zones, and λ is the wavelength of the light in a vacuum.

The change in focal length and focusing efficiency subsequently influences the reflected optical power when measured at a constant distance. Therefore, if reflected power is measured at a constant distance, it is possible to calculate glucose concentration. FIGS. 11A-13B illustrate experimental results that establish the correlation between reflected optical power of a glucose-responsive bifocal contact lens and glucose concentrations. More specifically, FIGS. 11A-11E are experimental results that illustrate the correlation between optical power of the lens and glucose concentration. And FIGS. 12A-13B are experimental results that illustrate the correlation between reflected optical power of the lens and glucose concentration.

Figure 4:
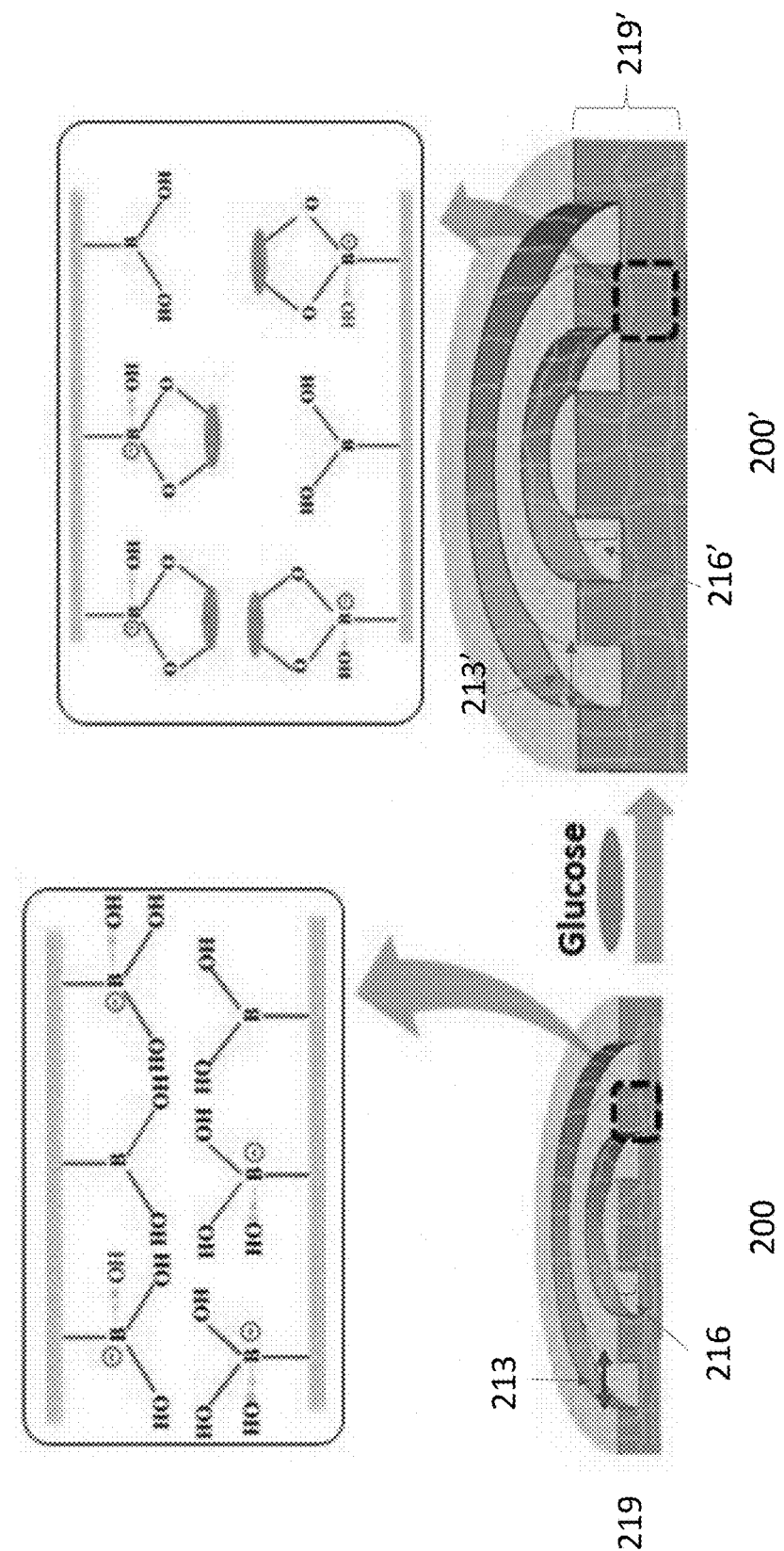
FIG. 4 is an illustration of a cross sectional-view of a glucose-responsive bifocal contact lens swelling in response to high glucose concentrations, according to one or more embodiments of the present disclosure.

FIG. 4 is a cross sectional-view of a glucose-responsive bifocal contact lens 200 and 200' swelling in response to high glucose concentrations. FIG. 4 is merely an exemplary illustration of the swelling phenomena and is not drawn to scale. Glucose-response bifocal contact lens 200 comprises a plurality of concentric rings 212, a groove depth 216, and a separation distance 213. Glucose-response bifocal contact lens 200 has a total thickness 219. Glucose-response bifocal contact lens 200' comprises a central zone 205', a plurality of concentric rings 212", a groove depth 216', and a separation distance 213'. Glucose-response bifocal contact lens 200 has a total thickness 219'.

The reaction between the relevant biomarker (glucose) and the biomarker-responsive compound immobilized within the hydrogel matrix (phenylboronic acid (PBA) derivative) causes the swelling phenomena. Groove depth increases (216'>216), separation distance increases (213'>213), and thickness increases (219'>219).

In other embodiments, different biomarker-responsive compounds may be immobilized within the hydrogel matrix to react with different biomarkers. For instance, lactate-responsive compounds may be immobilized within the hydrogel matrix to react with the lactate biomarker. In other embodiments, various protein recognition agents can be immobilized within the hydrogel matrix to detect various proteins.

In some embodiments for glaucoma detection, a change of cornea curvature can be detected using the developed structure of the bifocal contact lens. Indicators of glaucoma include increased corneal thickness, changes to corneal curvature, and increased intraocular (IOC) eye pressure. Changes to corneal thickness, corneal curvature, and IOC eye pressure will affect the interspace distance for the grooves of the attached Fresnel lens, altering the focal length and the optical performance of the attached Fresnel lens. Hence, in some embodiments, glaucoma can be detected without using any biomarker-responsive compound.

Figure 5A:
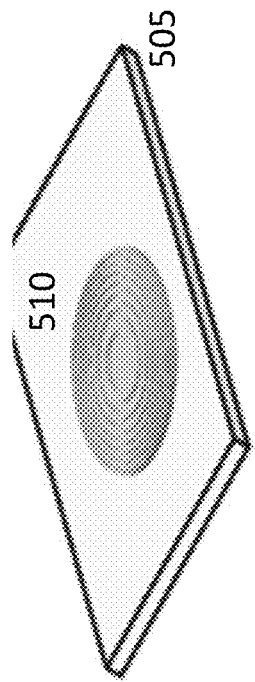
FIG. 5A is a perspective view of a Fresnel lens mold, according to one or more embodiments of the present disclosure.
Figure 5B:
FIG. 5B is a cross-sectional view of a Fresnel lens mold, according to one or more embodiments of the present disclosure.

The embodiments in FIGS. 5A-8B illustrate a method of manufacturing a biomarker-responsive bifocal contact lens comprising a series of steps. FIGS. 5A-5B show a perspective view and a cross-sectional view of a Fresnel mold 510 resting on flat slide 505. In one embodiment, Fresnel mold 510 is made from a PDMS hydrogel because of its hydrophobic surface properties that facilitate peeling off later in the manufacturing process. In other embodiments, the Fresnel mold 510 can be made from solid materials such as glass, plastic, rubber, or metal alloys that may include hydrophobic coatings to facilitate peeling. Flat slide 505 may be made from glass, or other solid materials such as plastic, rubber, or metal alloys.

FIGS. 6A-6B show a perspective view and a cross-sectional view of a Fresnel mold 510 resting on flat slide 505 and a biomarker-responsive gel 520 being cast onto the Fresnel mold 510. In the embodiment show in FIG. 6A, the biomarker-responsive gel is cast using a drop-casting method by dropping gel droplets onto the Fresnel mold 510 from a source 530. In other embodiments, different forms of casting may be used, such as high-pressure casting, low-pressure casting, centrifugal casting, or any other casting methods known in the art.

The biomarker-responsive gel 520 must contain a biomarker-responsive compound. For example, in the embodiment illustrated in FIGS. 2A-3C, a phenylboronic acid (PBA) derivative is immobilized in the hydrogel matrix. This biomarker-responsive compound reacts with the particular biomarker to alter the optical characteristics of the contact lens.

Figure 7A:
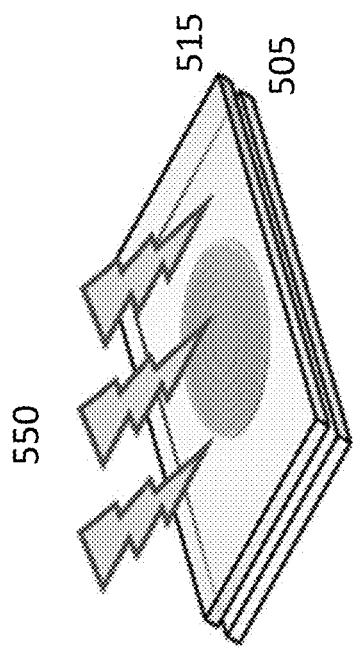
FIG. 7A is a perspective view of a polymerization of a biomarker-responsive hydrogel, according to one or more embodiments of the present disclosure.
Figure 7B:
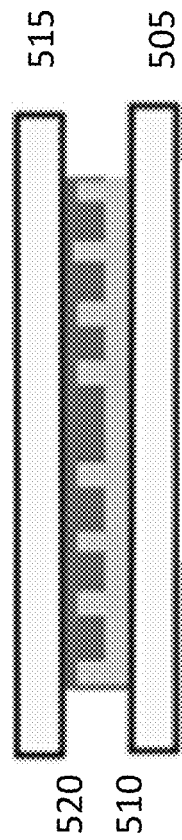
FIG. 7B is a perspective view of a polymerization of a biomarker-responsive hydrogel, according to one or more embodiments of the present disclosure.

FIGS. 7A-7B show a perspective view and a cross-sectional view of a Fresnel mold 510 resting on flat slide 505 with biomarker-responsive gel 520 being polymerized by UV rays 550. In some embodiments, the biomarker-responsive gel 520 undergoes a UV polymerization. The UV polymerization process can last between 5 minutes to 60 minutes, with light intensity in the range of 300 mW/cm² to 1000 mW/cm². The UV polymerization may include a top flat slide 515 placed onto the biomarker-responsive gel 520. In other embodiments, the biomarker-responsive gel 520 undergoes heat polymerization or any other hydrogel polymerization processes known in the art. The biomarker-responsive gel 520 subsequently turns into biomarker-responsive hydrogel 502 when the polymerization process is complete.

Figure 8A:
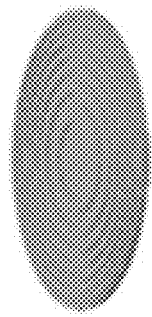
FIG. 8A is a perspective view of a biomarker-response hydrogel, according to one or more embodiments of the present disclosure.

FIG. 8A shows a perspective view of biomarker-responsive hydrogel 502. After the polymerization process is complete, flat slides 505 and 515 are removed, and biomarker-responsive hydrogel 502 is peeled off from the Fresnel mold 510. In other embodiments, Fresnel mold 510 is peeled off from the biomarker-responsive hydrogel 502.

Figure 8B:
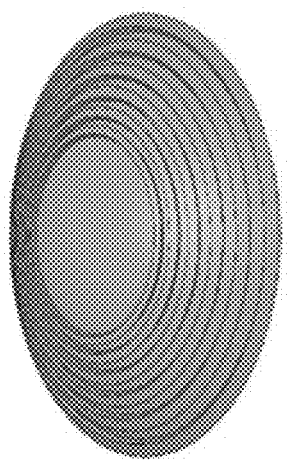
FIG. 8B is a perspective view of a biomarker-responsive bifocal contact lens, according to one or more embodiments of the present disclosure.

FIG. 8B shows a perspective view of biomarker-responsive bifocal contact lens 500. Biomarker-responsive hydrogel 502 is attached to a monovision contact lens (not shown here) having a substantially domed shape to fit a patient's eye. The substantially domed shape of the monovision contact lens gives the biomarker-responsive bifocal contact lens 500 its domed shape. In some embodiments, biomarker-responsive hydrogel is attached to monovision contact lens using an adhesive, pressure fit, or polymerization process. In other embodiments, monovision contact is attached during the biomarker-responsive gel 520 polymerization process illustrated in FIGS. 7A-7B.

FIG. 9 illustrates a method of measuring a biomarker concentration using a biomarker-responsive bifocal contact lens 600. The embodiment shown in FIG. 9 comprises a light source 650 that produces light beam 652 with a wavelength λ. Light beam 652 hits biomarker-responsive bifocal contact lens 600 at an angle $\theta_1$ and reflects off contact lens 600 at an angle $\theta_2$. Reflected light beam 662 is collected by the photodetector 660.

In one embodiment, light source 650 is disposed at a height $H_1$ above the center of contact lens 600 and a horizontal distance $D_1$ from the center of contact lens 600. Photodetector 660 is disposed at a fixed point at a height $H_2$ above the center of contact lens 600 and a horizontal distance $D_2$ from the center of contact lens 600. In some embodiments, photodetector 660 is at a constant distance X from the contact lens 600.

In some embodiments, the data photodetector 660 collects is transmitted to an electronic device (not shown) via a transmitter (not shown). The transmitted data is then processed by the electronic device and the biomarker concentration is calculated. After the biomarker concentration is calculated, the biomarker concentration is presented to the patient via audio or visual display. In other embodiments, photodetector 660 can house the electronic device, and all data analysis and calculation can be done by the electronic device within the photodetector.

As illustrated in the embodiment depicted in FIGS. 2A-3C, the reflected optical power of a biomarker-responsive contact lens peaks at the focal points. If, for example, a focal point shifts in response to changes in biomarker concentration, the peak also shifts. Therefore, it is desirable to measure the optical characteristics of reflected light beam 662 at a constant distance X from the biomarker-responsive contact lens. Analyzing the reflected optical power of reflected light beam 662 at constant distance X removes all outside variables from the equation and allows for accurate calculation of biomarker concentration (see Example section below for correlation of glucose concentration to reflected power at a constant distance of measurement).

Figure 10:
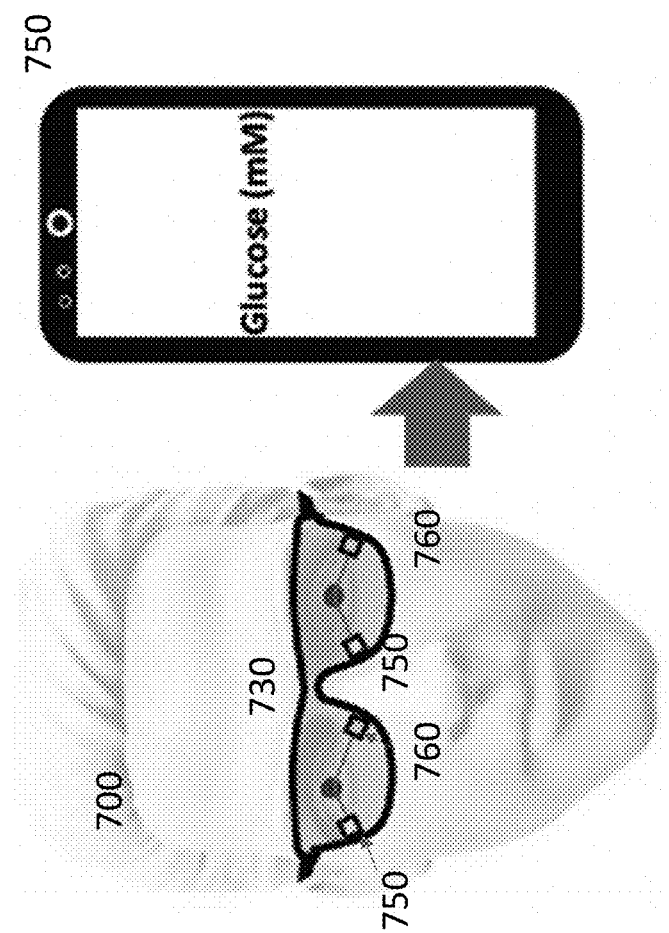
FIG. 10 is an illustration of a glasses with a laser and a photodetector installed in the glasses frame, according to one or more embodiments of the present disclosure.

FIG. 10 is one embodiment of the method illustrated in FIG. 9. Glasses frame 730 have a light source 750 and a photodetector 760 installed in the frame. A patient 700 wearing biomarker-responsive bifocal contact lenses (not shown here), wears the glasses frame 730, which produces light beam 752 with a wavelength λ. Laser beam 752 is hits biomarker-responsive bifocal contact lens at an angle $\theta_1$ and reflects off contact lens at an angle $\theta_2$. Reflected light beam 662 is collected by a photodetector 760.

In one embodiment, the data collected by photodetector 760 is transmitted to a smartphone device 770. The smartphone device 770 will receive the data and perform biomarker concentration calculation using the data. In other embodiments, the glasses frame 730 will transmit data to other external devices such as a computer, tablet, television, or any other electronic device capable of analyzing the data.

In other embodiments, glasses frame 730 may include a processing component to analyze the data. Glasses frame 730 may also include a display or audio component to inform the patient of a biomarker concentration.

EXAMPLES

Example 1—Physical Testing

This experiment investigated the influence of the Fresnel lens structural dimensions on the contact lens response. Four glucose-responsive Fresnel lenses were fabricated: i) free-standing lens with FL-25 imprinted on its surface (FS-25), ii) glass-constrained lens with FL-25 replicated on its surface (GC-25), iii) free-standing lens with FL-10 replicated on its surface (FS-10), and v) glass-constrained lens with FL-10 replicated on its surface (GC-10). Imprinting both Fresnel lenses of different groove spacing 0.25 mm (f=25 mm), and 0.1 mm (f=10 mm) on the hydrogel sensors allowed for investigating the influence of the optical transducer's dimensions on the sensor's performance.

To examine the lens' response, glucose concentrations (0-25 mm) were prepared in phosphate buffer saline (PBS) solutions (pH 7.4, ionic strength: 150 mm) and the sensors were equilibrated for 24 hours in glucose-free PBS solution prior to testing. Any changes in refractive index, groove spacing, and the number of concentric ring zones (m) resulting from the glucose-boronate interaction influences the optical performance of the Fresnel lens; focus efficiency, focal length, and subsequently, the optical power measured at an identical distance. Analysis was conducted by recording the optical power for the laser beam after passing through the lens at a distance greater than focal length. Optical power detection was utilized instead of the changes in the focal length as it was favorable in terms of practicality, which rendered the readout methodology simple. In addition, according to the literature, the focal length changes would be slight, which may not allow accurate detection in sensing applications.

The FS-25 glucose sensitive lens was immersed in glucose-free PBS (1 mL) and the optical power of the laser beam was detected at 25 cm away from the sensor. The measurements were repeated while the sensor was submerged in various glucose concentrations (0-10 mm) starting from low to high concentrations with an increment step of 2.5 mm glucose, and a step of 5 mm at a higher glucose range (10-25 mm). Upon introducing the glucose solution, the lens swelled due to 1:1 glucose-boronate binding. PBAs have an affinity to reversibly bind with 1,2-diols such as glucose, and 1,3-diols forming either 1:1 complex or 2:1 crosslinking. In 1:1 PBA-glucose complexation, Donnan potential is induced causing osmatic pressure, which swells the hydrogel matrix, while 2:1 complexation leads to shrinkage of the hydrogel matrix due to the extra crosslinks resulting from boronate-glucose interaction.

The present lens is designed to operate at the physiological pH (7.4), which is lower than the pKa of the utilized boronic acid, 3-(acrylamido) phenylboronic acid (pKa=8.5) when it is incorporated in the polyacrylamide hydrogel. At low pH, PBA exists in an uncharged trigonal planar form that reacts with glucose forming cyclic ester of pKa less than the physiological pH, subsequently it dissociates into a hydrogen ion and a stable boronate anion. While at high pH>pKa, the trigonal configuration of PBA dissociates donating a proton to constitute a stable tetrahedral anion, which has high affinity and stability to bind with glucose.

Figures 11A, 11B:
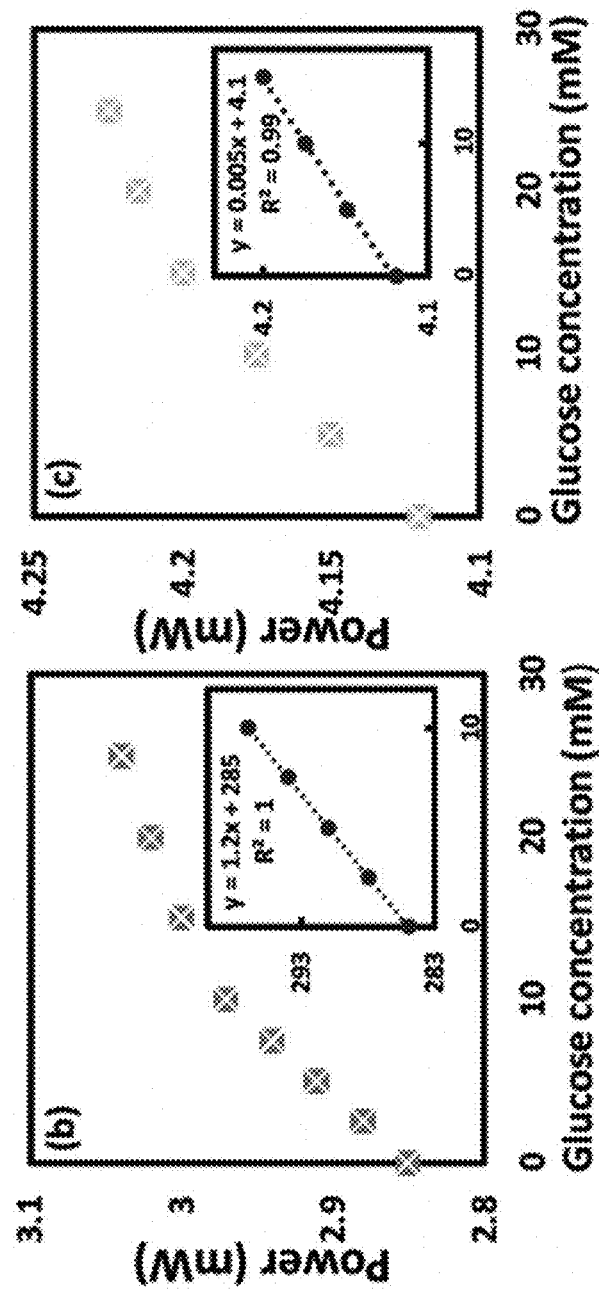
FIG. 11A is a graphical illustration of transmitted optical power versus glucose concentration for an FS-25 glucose-responsive lens, according to one or more embodiments of the present disclosure.
FIG. 11B is a graphical illustration of transmitted optical power at different glucose concentrations for an GC-25 glucose-responsive lens, according to one or more embodiments of the present disclosure.
Figures 11C, 11D, 11E:
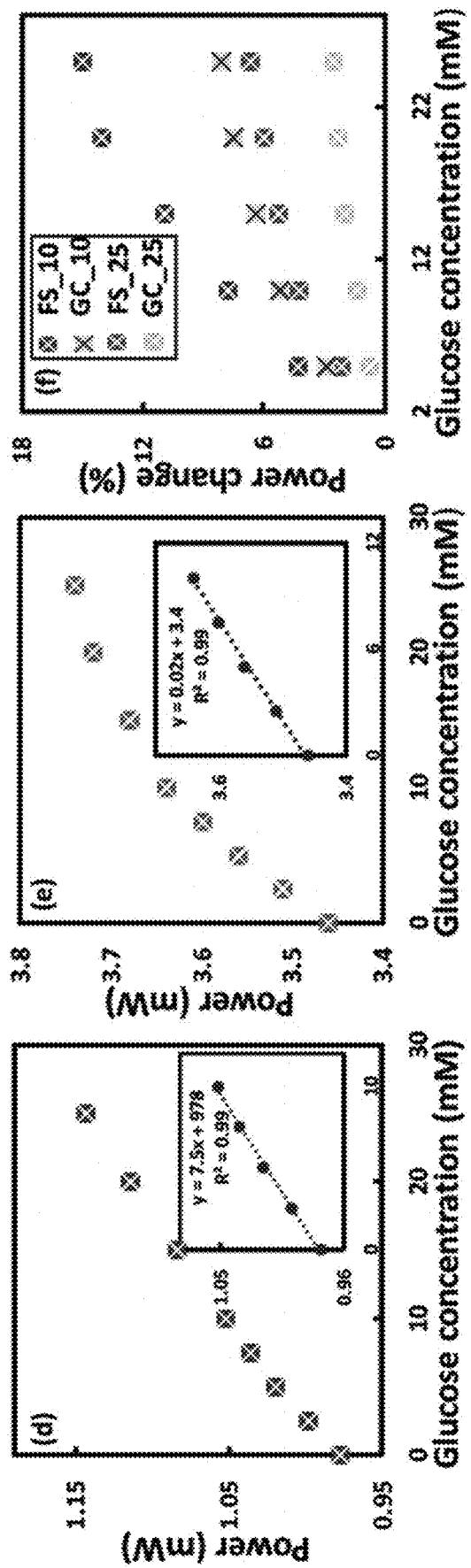
FIG. 11C is a graphical illustration of transmitted optical power versus glucose concentration for an FS-10 glucose-responsive lens, according to one or more embodiments of the present disclosure.
FIG. 11D is a graphical illustration of transmitted optical power versus glucose concentration for an GC-10 glucose-responsive lens, according to one or more embodiments of the present disclosure.
FIG. 11E is a graphical illustration of percent change of the recorded power for the four glucose lenses at different glucose concentrations, according to one or more embodiments of the present disclosure.

Results: The FS-25 lens expanded in 3D, decreasing the number of concentric ring zones (m) exposed to the laser beam, and consequently increasing the focal length. Hence, FIG. 11A shows the transmitted recorded optical power at a distance greater than the focal length increased with glucose concentration. Furthermore, the sensor's refractive index decreased when the hydrogel sensor swelled resulting from imbibing a more aqueous solution, which has lower refractive index than the hydrogel matrix. The lens presented a linear response within the glucose range of 0-10 mm, that had a correlation coefficient R2=1. However, the sensitivity decreased with increasing glucose concentration. The sensitivity of the sensor in the low glucose range (0-10 mm) was 12 µW mm-1. However, the change in the measured optical power with glucose concentration depended on the initial power that illuminated the lens in glucose-free solution.

FIGS. 11B-11E show it was more accurate to rely on the percentage change of the measured power which was found to be 0.42% mm-1 for FS-25 lens and 0.13% mm-1 for the GC-25 lens. The sensitivity of the free-standing lens was almost threefold that of its counterpart, the glass-constrained lens (GC-25). This difference is attributed to swelling the lens in the surface's paralleled plane, which allows for changing the diameter of the concentric rings, and hence the groove spacing. Additionally, the expansion of the free-standing lens in 3D rendered the lens capable of absorbing more aqueous solution and consequently, a more decrease in its refractive index was expected. The sensitivity of the FS-10 lens in the low glucose concentration range (0-10 mm) was 0.77% mm-1 which was almost double the sensitivity of that of FS-25; however, both lenses were made of the same glucose-responsive hydrogel. These results reflected the significance of the dimensions of the employed optical transducers for monitoring the dynamic volumes. It can be concluded that the tenuous volumetric changes could be detected by a minute or nanoscale transducer. Also, GC-10 lens showed a sensitivity of 0.52% mm-1 which was higher than that of both FS-25 and GC-25 lenses in the same glucose range (0-10 mm) (see FIGS. 11D-E). Furthermore, at high glucose concentrations (10-25 mm), GC-25 lenses saturated; however, the GC-10 lens was still capable of detecting the subtle volumetric shifts. These results indicate that dimensions of the glucose-responsive lens influence not only the sensitivity but also the detection range of the lens.

Example 2—Physical Testing

Further investigations were carried out for glass-constrained lenses. The two glucose-responsive lenses; GC-25 and GC-10 were interrogated for glucose sensing in reflection configuration as a practical mode. A lens was immersed in a Petri dish while the Fresnel structure facing up the incident laser beam, which hit the surface at an inclined angle of 45° and the reflected beam was collected at 45° from the other side. The photodetector was fixed at 30 cm away from the sample's surface and the reflected signal was recorded continuously over time.

Figure 12B:
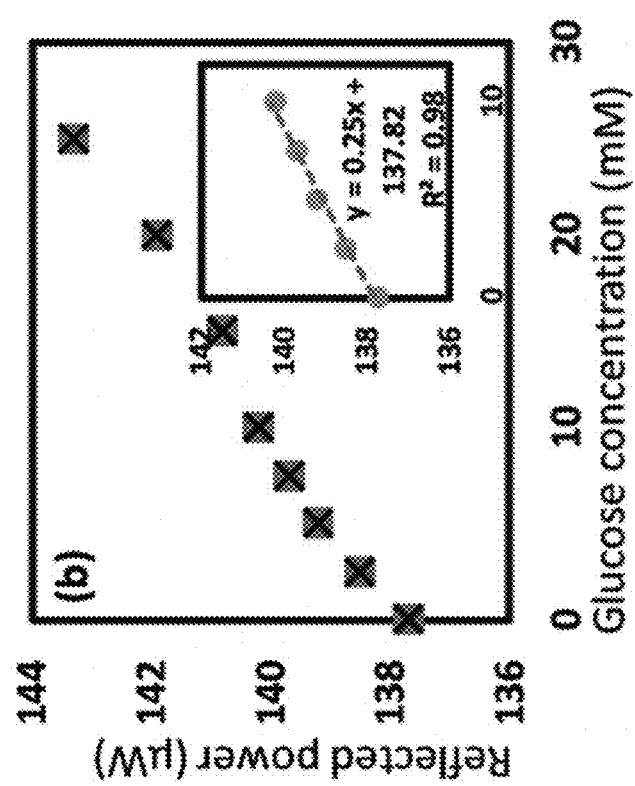
FIG. 12B is a graphical illustration of reflected optical power from the GC-10 lens when the lens was immersed in various glucose concentrations, according to one or more embodiments of the present disclosure.
Figure 12A:
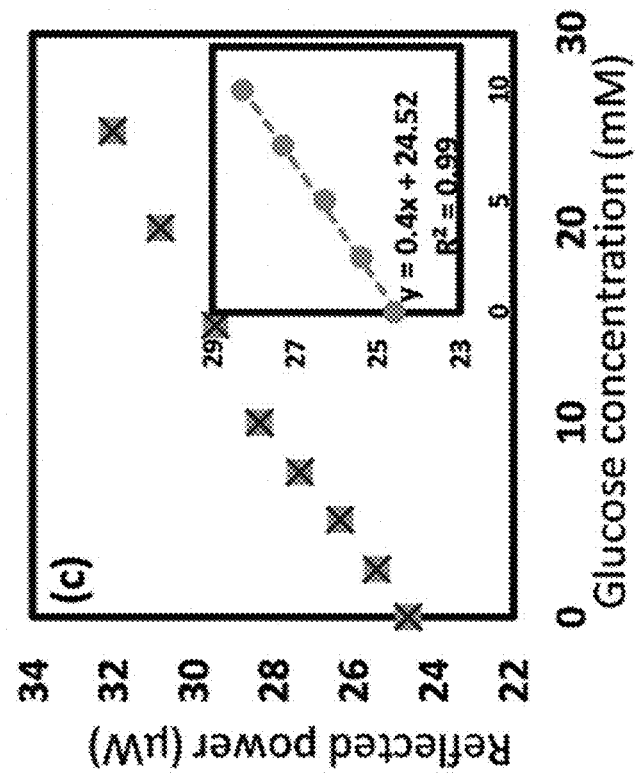
FIG. 12A is a graphical illustration of reflected optical power from the GC-25 lens when the lens was immersed in various glucose concentrations, according to one or more embodiments of the present disclosure.
Figure 12C:
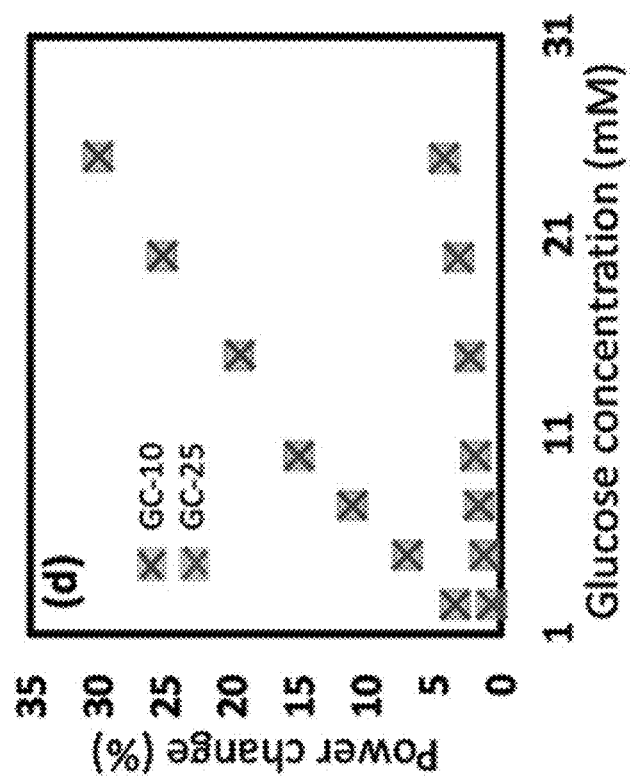
FIG. 12C is a graphical illustration of percent power change from the GC-10 lens and the GC-25 lens when the lens were immersed in various glucose concentrations, according to one or more embodiments of the present disclosure.

Results: FIGS. 12A-B shows both GC-25 and GC-10 lenses had similar trends in response to the increase of glucose concentration. As FIG. 12C illustrates, when the glucose concentration increased from 0 to 10 mm, the reflected optical power positively shifted by 1.8%, and 15% for the GC-25 and GC-10, respectively. In contrast to the transmission mode measurements, the GC-25 lens in reflection mode showed a response for low glucose concentration (2.5 mm), which could not be detected in transmission configuration, and the saturation response at a high glucose concentration range (10-25 mm) was not observed.

Furthermore, the sensitivity increased by ≈38% and 200% for the GC-25 and GC-10 lenses, respectively. These enhancements may be attributed to the advantages of the inclined incident angle of the laser beam in the reflection configuration setup. The superior sensitivity of the GC-10 lens (15%) in the same glucose range might be attributed to the finer dimensions of the Fresnel lens (FL-10). In addition, the optical performance of the FL-10 was sensitive for subtle changes of its refractive index and groove depth. To show the capability of the GC-10 lens to function at low glucose concentration at physiological range in tears, it was interrogated in the glucose concentration range of 0.0-3.3 mm. The lens showed a linear response, sensitivity of 6.7% for the whole glucose range, and a low LOD of 0.51, which reflect its robust performance.

Example 3—Physiological Condition Testing

Figures 13A, 13B:
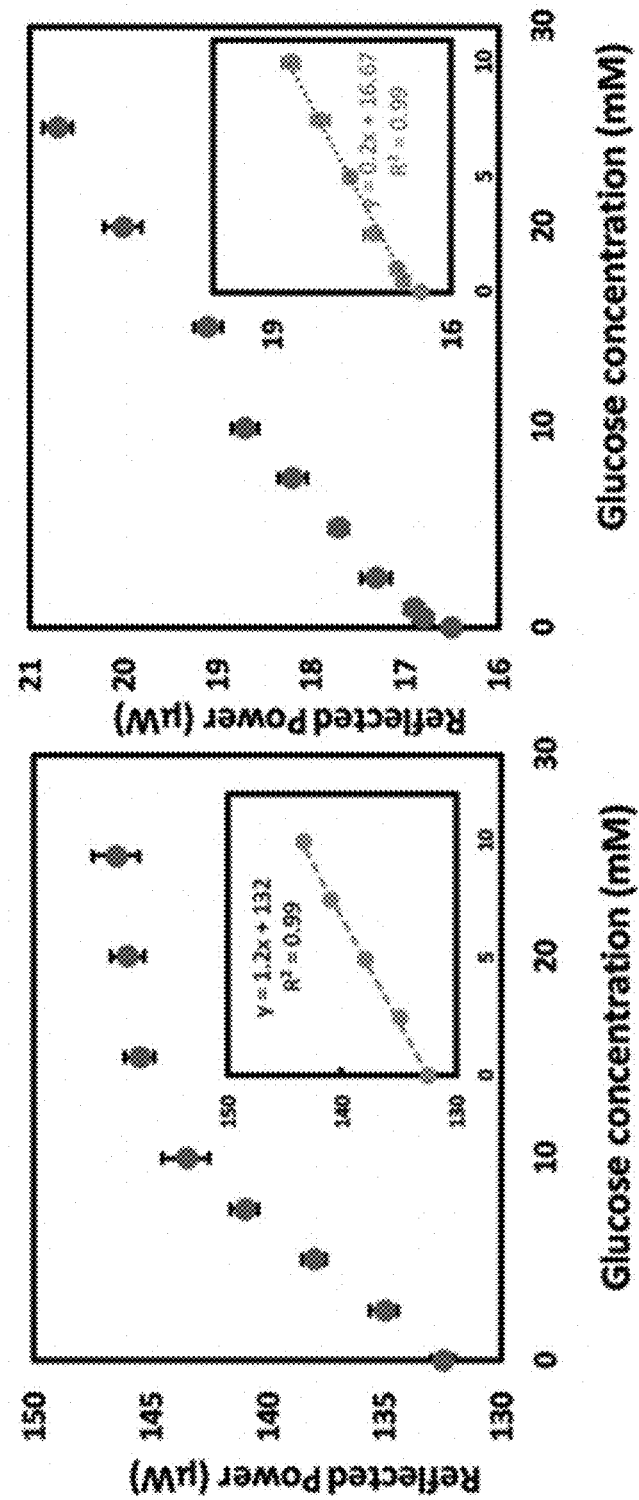
FIG. 13A is a graphical illustration of reflected optical power from the bifocal contact lens CL-25 when the lens was immersed in various glucose concentrations, according to one or more embodiments of the present disclosure.
FIG. 13B is a graphical illustration of reflected optical power from the bifocal contact lens CL-25 when the lens was immersed in various glucose concentrations, according to one or more embodiments of the present disclosure.

The contact lenses loaded with the glucose-responsive hydrogel were tested for glucose detection in reflection configuration under physiological conditions (pH 7.4, ionic strength: 150 mm, 37° C.) (See FIGS. 13A-B). The CL-25 lens was interrogated at 37° C., showing a linear response for the glucose concentration range of 0-10 mm similar to the GC-25 lens tested in reflection mode at room temperature (24°). However, at a high glucose concentration range (10-25 mm), the CL-25 saturated. This was indicated by the subtle shift in the detected signals as the measured power increased by 2.9 µW while for the low glucose range (0-10 mm) the power increased by 11 µW. It can be concluded that at physiological temperature (37° C.), the sensitivity of the lens significantly declined at high glucose concentrations (10-25 mm) than when the glucose test was carried out at room temperature (24° C.). The response of the CL-10 for glucose at 37° C. supported this conclusion as the sensitivity of the CL-10 for glucose concentration range of 10-25 mm was 10.7% compared to 13% for the GC-10 tested at 24° C. The LOD for the CL-25 was found to be 2.5 mm, which was above the range of glucose concentration in tears for healthy individuals (0-1.1 mm); however, glucose concentration for diabetic patients can increase up to 3.3 mm. In contrast, the CL-10 was able to detect glucose concentration in healthy people range showing a LOD 0.5 mm (FIG. 13B). Utilizing Fresnel lenses of smaller groove spacing<0.1 mm can enable developing a glucose sensor with a lower LOD (≈0.1 mm).

In conclusion, a relationship was confirmed between glucose concentrations and reflected optical power of the glucose-responsive contact lens. Furthermore, the glucose-responsive contact lens is able to operate under standard physiological conditions.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A biomarker-responsive bifocal contact lens, the biomarker-responsive bifocal contact lens comprising:
   a monovision contact lens having a first focal length; and
   a Fresnel contact lens having a second focal length, wherein the Fresnel contact lens comprises a biomarker-responsive hydrogel, and wherein the Fresnel contact lens is disposed on an outer surface of the monovision contact lens,
   wherein an optical characteristic of the Fresnel contact lens changes in response to the biomarker concentration in the ocular fluid.

2. The biomarker-responsive bifocal contact lens of claim 1, wherein the relevant biomarker is glucose.

3. The biomarker-responsive bifocal contact lens of claim 2, wherein the Fresnel contact lens comprises a phenylboronic acid derivative responsive to a glucose concentration.

4. The biomarker-responsive bifocal contact lens of claim 1, wherein the optical characteristic includes a focus efficiency, a focal length, an optical power, a separation distance of concentric rings, a groove depth, or a refractive index.

5. The biomarker-responsive bifocal contact lens of claim 1, wherein the Fresnel contact lens has a central zone to enable far-viewing.

6. The biomarker-responsive bifocal contact lens of claim 1, wherein the biomarker-responsive contact lens undergoes a swelling response when exposed to biomarker.

7. The biomarker-responsive bifocal contact lens of claim 1, wherein the relevant biomarker is a glaucoma biomarker.

8. A method of manufacturing a biomarker-responsive bifocal contact lens, the method comprising the steps of:
   providing a Fresnel lens mold;
   casting a biomarker-responsive gel on the Fresnel lens mold, the biomarker-responsive gel comprising a biomarker-responsive compound;
   polymerizing the biomarker-responsive gel, wherein the biomarker-responsive gel is converted into a biomarker responsive hydrogel;
   removing the biomarker-responsive hydrogel from the Fresnel lens mold; and
   combining the biomarker-responsive hydrogel with a monovision contact lens.

9. The method of claim 8, wherein the polymerization step includes a UV polymerization.

10. The method of claim 8, wherein the polymerization step includes a heat-assisted polymerization.

11. The method of claim 8, wherein the monovision contact lens in combined with the biomarker-responsive hydrogel before the polymerization step.

12. The method of claim 8, wherein the biomarker-responsive hydrogel includes a phenylboronic acid derivative responsive to a glucose concertation.

13. The method of claim 8, wherein the Fresnel lens mold has hydrophobic properties.

14. A method of measuring a biomarker concentration using a biomarker-responsive bifocal contact lens, the method comprising:
   placing the biomarker-responsive bifocal contact lens on an eye of a patient, the biomarker-responsive bifocal contact lens comprising:
      a monovision contact lens having a first focal length; and
      a Fresnel contact lens having a second focal length, wherein the Fresnel contact lens is formed from a biomarker-responsive hydrogel,
   operating a light source at an angle $\theta$ incident to the contact lens, wherein a laser beam hits the contact lens as the angle $\theta$ and reflects off of the contact lens;
   collecting a reflected light beam in a photodetector at a constant distance X from the contact lens;
   measuring an optical characteristic of the reflected light beam; and
   calculating the biomarker concentration.

15. The method of claim 14, wherein the optical characteristic comprises a focus efficiency, a focal length, an optical power, a separation distance of concentric rings, a groove depth, or a refractive index.

16. The method of claim 14, wherein data collected by the photodetector is transmitted to an external device.

17. The method of claim 16, wherein the external device analyzes the data and calculates the biomarker concentration.

18. The method of claim 17 wherein the external device displays the biomarker concentration.

19. The method of claim 14, wherein the light source and the photodetector are installed in a glasses frame.

20. The method of claim 14, wherein the Fresnel contact lens is formed from a glucose-responsive hydrogel.

* * * * *